US008679377B2

(12) United States Patent
Munro, III et al.

(10) Patent No.: US 8,679,377 B2
(45) Date of Patent: Mar. 25, 2014

(54) GAMMA RADIATION SOURCE (71) Applicants: John J. Munro, III, North Andover, MA (US); Kevin J. Schehr, New Orleans, LA (US)

(72) Inventors: John J. Munro, III, North Andover, MA (US); Kevin J. Schehr, New Orleans, LA (US)

(*) Notice: Subject to any disclaimer, the term of this patent is extended or adjusted under 35 U.S.C. 154(b) by 0 days.

(21) Appl. No.: 13/705,277

(22) Filed: Dec. 5, 2012

(65) Prior Publication Data
US 2013/0302236 A1    Nov. 14, 2013

Related U.S. Application Data (62) Division of application No. 12/586,779, filed on Sep. 28, 2009, now Pat. No. 8,357,316.

(51) Int. Cl.
*C01B 19/02* (2006.01)
*G21G 4/00* (2006.01)
*G21G 4/08* (2006.01)

(52) U.S. Cl.
USPC ........... 252/644; 252/645; 423/508; 423/509; 423/249; 420/1; 420/579; 250/493.1; 250/494.1

(58) Field of Classification Search
USPC .................. 252/644, 645; 423/508, 509, 249; 420/1, 579; 250/493.1, 494.1
See application file for complete search history.

(56) References Cited

U.S. PATENT DOCUMENTS

| | | | |
|---|---|---|---|
| 3,234,099 A * | 2/1966 | Tonks et al. | 376/189 |
| 6,875,377 B1 | 4/2005 | Shilton et al. | |
| 8,357,316 B2 * | 1/2013 | Munro et al. | 252/645 |

FOREIGN PATENT DOCUMENTS

RU    2196363 C2    10/2003

OTHER PUBLICATIONS

EPO Search Report/Communication, dated Dec. 20, 2010. Shilt reference provided in prior IDS, Russian reference attached herein with trans.
Arai, D, et al., "Network dynamics of chalcogenide glasses II. Silicon diselenide," Phys. Rev., B 37, 4240-4245 (1988).
Bletskan, D.I., "Phase Equilibrium in the biniary systems AIVBVI, Part I. The systems Silicon-Chalcogen," Journal of Ovonic Research, vol. 1, No. 5, Oct. 5, 47-52.
Johnson, R.W., et al., "Preparation and characterization of SixSe I x Glasses and determination of the equilibrium phase diagram," Mat. Rs. Bull., vol. 21, 41-47, 1986.
Ross, L., et al., "The germanium—selenium phase diagram," Canadian Journal of Chemistry, Vo. 47, pp. 2555-2559, 1969.
Kaldis, et. al., "A solid state chemistry of new semiconductors with valance instabilities: TmSe1-x and Tm1-xEuxSe," J. Phys. Colloques, vol. 41, C5-135 to C5-142, 1980.
Matsumura, T., et al., "Low temperature properties of the magnetic semiconductor TmTe," J. Phys. Soc., Japan, vol. 67, 612-621, 1998.

* cited by examiner

*Primary Examiner* — Timothy Vanoy
(74) *Attorney, Agent, or Firm* — Stan Collier, Esq.

(57) ABSTRACT

A gamma radiation source comprises $^{75}$Selenium wherein the $^{75}$Selenium is provided in the form of compounds, alloys or mixtures with one or more nonmetals which upon irradiation do not produce products capable of sustained emission of radiation which would unacceptably interfere with the gamma radiation of $^{75}$Selenium. A further gamma radiation source comprises $^{75}$Selenium wherein the $^{75}$Selenium is provided in the form of compounds, alloys or mixtures with one or more metals or nonmetals, the neutron irradiation of which does produce products capable of sustained emission of radiation which would acceptably complement the gamma radiation of $^{75}$Selenium. Further, the gamma radiation source may have components that are separately irradiated before being combined and the components may be of natural isotopic composition or of isotopically modified composition so that the subsequent radiation peaks may also be adjusted in relative frequency.

5 Claims, 6 Drawing Sheets

FIG. 2E  $^{75}$Selenium and $^{192}$Iridium

FIG. 2F  $^{65}$Zinc

FIG. 2G  $^{75}$Selenium and $^{65}$Zinc

FIG. 3

GAMMA RADIATION SOURCE

CROSS-REFERENCES TO RELATED APPLICATIONS

This is a divisional application of Ser. No. 12/586,779, issued as U.S. Pat. No. 8,357,316 on Jan. 22, 2013, being entitled Gamma Radiation Source by the same inventors.

REFERENCE TO FEDERALLY SPONSORED RESEARCH OR DEVELOPMENT

NA

REFERENCE TO JOINT RESEARCH AGREEMENTS

NA

REFERENCE TO SEQUENCE LISTING

NA

BACKGROUND OF THE INVENTION

1. Field of the Invention

The present invention relates generally to radiation testing and medical treatment, and, in particular, relates to radiation testing and the medical treatment using gamma radiation sources, and, in greater particularity, relates to radiation testing and medical treatment using $^{75}$Selenium.

2. Description of the Prior Art

The use of radioactive sources in present technology is an important feature as compared to x-rays, for example, in that radioactive sources can be tailored to specific uses. These sources may emit particle and/or wave radiation of varying energies in the spectrum and further have half-lives from mere seconds to years. Since some of these elements are extremely reactive, processing these sources into useable products is a critical and complex task to protect users and minimize manufacturing costs.

U.S. Pat. No. 6,875,377 describes the specific problem of combining $^{75}$Selenium with an acceptable metal source:

"In the past, $^{75}$Selenium sources have been made by encapsulating elemental $^{74}$Selenium target material inside a welded metal target capsule. This is irradiated in a high flux reactor to convert some of the $^{74}$Selenium to $^{75}$Selenium. Typically, target capsules are made of low-activating metals, such as aluminum, titanium, vanadium and their alloys. Other expensive metals and alloys are also possible. The use of these metals ensures that impurity gamma rays arising from the activation of the target capsule are minimized. The $^{75}$Selenium is typically located within a cylindrical cavity inside the target capsule in the form of a pressed pellet or cast bead. To achieve good performance in radiography applications it is necessary for the focal spot size to be as small as possible and the activity to be as high as possible. This is achieved by irradiating in a very high neutron flux and by using very highly isotopically enriched $^{74}$Selenium target material, typically >95% enrichment.

After the irradiation, the activated target capsule is welded into one or more outer metal capsules to provide a leak-free source, which is free from external radioactive contamination.

Elemental selenium is chemically and physically volatile. It melts at 220° C. and boils at 680° C. It reacts with many metals, which might be suitable as low-activating capsule materials at temperatures above about 400° C.; this includes titanium, vanadium and aluminum and their alloys. Selenium may react explosively with aluminum. This means that careful choice of target capsule material is required and the temperature of the target capsule during irradiation must be kept below about 400° C. to prevent the selenium reacting with, and corroding the target capsule wall. If this occurred, it would increase the focal spot size, distort the focal spot shape and reduce the wall thickness and strength of the target capsule."

A solution is offered in U.S. Pat. No. 6,875,377 which is incorporated by reference:

"An embodiment of the present invention is to provide a source having a selenium target composition, which overcomes or ameliorates one or more of the problems associated with the use of elemental selenium, specifically the problems of achieving a thermally stable, non-volatile, non-reactive, high density, stable selenium target which nevertheless contains a very high density of selenium, comparable with the elemental form of the material.

The invention provides; in one of its aspects, a gamma radiation source comprising $^{75}$Selenium or a precursor thereof, wherein the selenium is provided in the form of one or more thermally stable compounds, alloys, or mixed metal phases with one or more metals (hereinafter referred to as acceptable metals or an acceptable metal) the neutron irradiation of which does not produce products capable of sustained emission of radiation which would unacceptably interfere with the gamma radiation of $^{75}$Selenium."

A definition of what is an "acceptable" metal is also provided in U.S. Pat. No. 6,875,377:

"Thus, for example, an acceptable metal, such as vanadium or rhodium, is activated but has no interfering gamma radiation. Molybdenum produces molybdenum-99 that does have interfering gamma radiation, but is very short lived and is therefore also an acceptable metal. Again, Thorium produces palladium-233 [appears to be an error in that thorium produces protactinium-233] having a 27 day half life, but the gamma radiation of palladium-233 is 300-340 keV which is very similar to selenium-75 and therefore acceptable."

The above U.S. Patent lists "acceptable metals":

"Preferably, the said acceptable metal or metals is from the group comprising vanadium, molybdenum, rhodium, niobium, thorium, titanium, nickel, lead, bismuth, platinum, palladium [see not above], aluminum, or mixtures thereof. More preferably, the said acceptable metal or metals comprises one or a mixture of vanadium or molybdenum or rhodium."

Accordingly, there is an established need for radiation sources that would complement present sources that would provide additional benefits.

SUMMARY OF THE INVENTION

The present invention is directed at a gamma radiation source having one or more zones of complementary radiation.

The present invention has a primary source of radiation contained within a primary radiation zone. A supplemental radiation source may be contained within a supplemental radiation zone that is centered on or about the primary radiation zone. A complementary radiation source is contained either in a lower radiation zone or an upper radiation zone. It should further be understood that during manufacturing of the gamma radiation source components may be irradiated separately before being combined so that subsequent radiation peaks may be adjusted in relative frequency. It should be further understood that the components may be of natural isotopic composition or of isotopically modified composition (enriched or depleted in certain isotopes) so that the subsequent radiation peaks may also be adjusted in relative frequency.

In the present invention, a gamma radiation source comprises $^{75}$Selenium or a precursor thereof, wherein the $^{75}$Selenium is provided in the form of one or more thermally stable compounds, alloys or mixtures with one or more nonmetals, the neutron irradiation of which does not produce products capable of sustained emission of radiation which would unacceptably interfere with the gamma radiation of $^{75}$Selenium. A further gamma radiation source comprises $^{75}$Selenium or a precursor thereof, wherein the $^{75}$Selenium is provided in the form of one or more thermally stable compounds, alloys or mixtures with one or more metals or nonmetals, the neutron irradiation of which does produce products capable of sustained emission of radiation which would acceptably complement the gamma radiation of $^{75}$Selenium.

An embodiment of the present invention is to provide a gamma radiation source having an adjustable radiation pattern for use in industry, research and medicine.

It is another embodiment of the present invention to provide a gamma radiation source having supplemental and/or complementary radiation components.

It is another embodiment of the present invention to provide one or more components being of natural isotopic composition or of isotopically modified composition (enriched or depleted in certain isotopes) so that the subsequent radiation peaks may also be adjusted in relative frequency.

It is a further embodiment of the present invention to provide a gamma radiation source based upon $^{75}$Selenium.

It is still a further embodiment of the present invention to provide a gamma radiation source having one or more nonmetal radiation components therein.

It is still a further embodiment of the present invention to provide a gamma radiation source based upon $^{75}$Selenium and having one or more nonmetal radiation components therein.

It is yet a further embodiment of the present invention to provide a gamma radiation source having one or more metallic and/or nonmetallic components therein.

It is yet a further embodiment of the present invention to provide a gamma radiation source based upon $^{75}$Selenium having one or more metallic and/or nonmetallic components therein.

These and other embodiments, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

The present invention is directed at a gamma radiation source based upon $^{75}$Selenium and one or more other gamma radiation sources or components combined into a single source having a unique gamma radiation spectrum.

Figure 1:
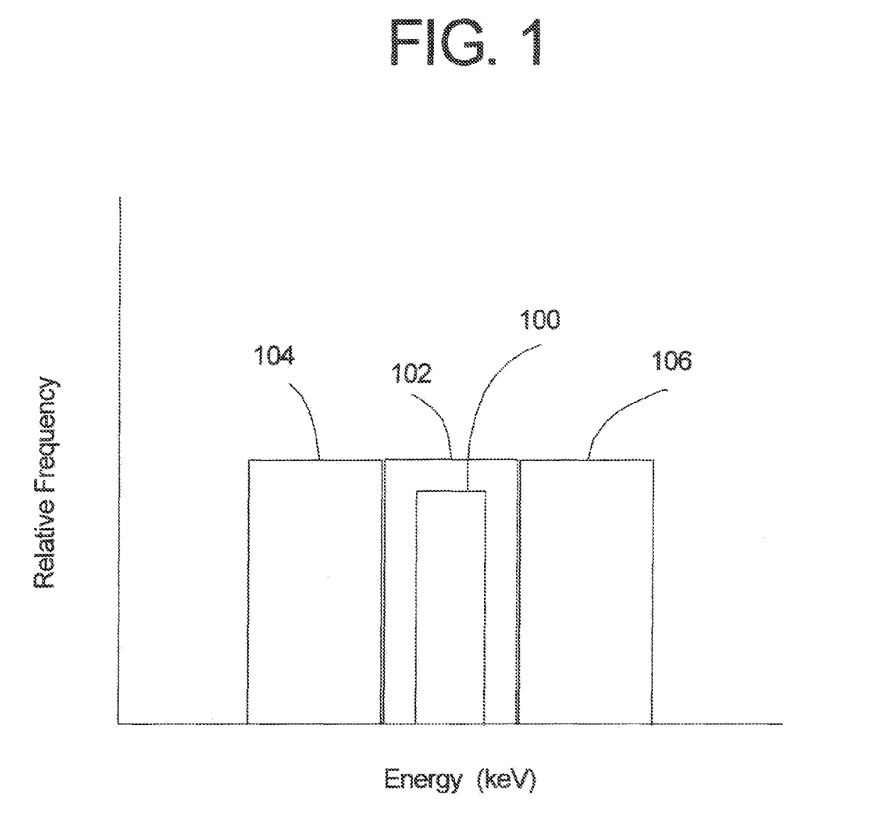
FIG. 1 is an energy graph illustrating different radiation patterns/zones in relation to a primary source zone of radiation.

Turning to the drawings, wherein like components are designated by like reference numerals throughout the various figures, attention is initially directed to FIG. 1 which illustrates an energy graph of different radiation source patterns/zones according to the present invention.

As best shown in FIG. 1, a primary source of radiation is essentially contained within a primary radiation zone 100. A supplemental radiation source is contained within a supplemental radiation zone 102 that is centered on or about the primary radiation zone 100. A complementary radiation source is contained either in a lower radiation zone 104 or an upper radiation zone 106. Supplemental means that it adds to the primary radiation, and complementary means it is additional radiation but not necessarily within the primary radiation zone 100. Although zones are shown in FIG. 1, it should be understood that peaks at different energies may fall outside that zone, but substantially all of the radiation falls within that zone as will be understood from the following discussion and figures. It should further be understood that during manufacturing of the gamma radiation source components of such may be irradiated separately before being combined so that subsequent radiation peaks may be adjusted in relative frequency. It should be further understood that the components may be of natural isotopic composition or of isotopically modified composition (enriched or depleted in certain isotopes) so that the subsequent radiation peaks may also be adjusted in relative frequency.

Nonmetallic Compounds

Figure 2A:
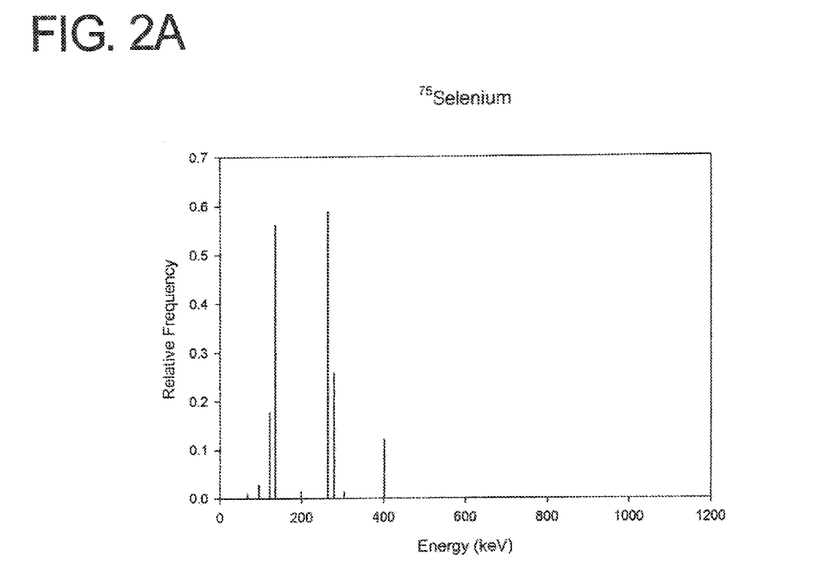
FIG. 2A is graph of the energy spectrum for $^{75}$Selenium.

There exist a number of nonmetals, the neutron irradiation of which does not produce products capable of sustained emission of radiation which would unacceptably interfere with the gamma radiation of $^{75}$Selenium, FIG. 2A, that can be combined with Selenium to form a thermally-stable compound or mixture.

Silicon Diselenide (SiSe$_2$)

One example is the chemical compound Silicon Diselenide (SiSe$_2$). Silicon is a nonmetal, sometimes referred to as a metalloid (an element with properties intermediate between those of a metal and nonmetal). Silicon diselenide is a compound with a melting temperature of 960° C. (Ref: M. Arai, D. L. Price, S. Susman, K. J. Volin, and U. Walter, Network dynamics of chalcogenide glasses. II. Silicon diselenide, Phys. Rev. B 37, 4240-4245 (1988). Bletskan, in (D. I. Bletskan, PHASE EQUILIBRIUM IN THE BINARY SYSTEMS $A^{IV}B^{VI}$, Part. I. The systems Silicon-Chalcogen, Journal of Ovonic Research Vol. 1, No. 5, October 2005, p. 47-52) describes the process for manufacturing $SiSe_2$. A more complete description is provided by Johnson et al (R. W. Johnson, S. Susman, J. McMillan, and K. J. Volln, PREPARATION AND CHARACTERIZATION OF SixSe 1 x GLASSES AND DETERMINATION OF THE EQUILIBRIUM PHASE DIAGRAM, Mat. Res. Bull., Vol. 21, pp. 41-47, 1986).

Natural (non-enriched) silicon can be used because neutron irradiation of natural silicon does not produce products capable of sustained emission of radiation. The longest-lived activation product is $^{31}$Silicon. Silicon with a half-life of only 2.6 hours. The use of isotopically-enriched or isotopically depleted Silicon would also be acceptable.

Germanium Selenide

There exist two selenides of Germanium (another non-metal metalloid): GeSe that melts at 670° C. and GeSe2, which melts at 740° C. (L. Ross and M. Bourgon, The germanium-selenium phase diagram, Canadian Journal of Chemistry, Vol. 47, pp 2555-2559, 1969).

There are only two isotopes of Germanium that are capable of sustained emission. $^{68}$Germanium has a half-life of 275 days, but is not produced by the neutron irradiation of any of the stable Germanium isotopes. $^{71}$Germanium, which is produced by the neutron irradiation of $^{70}$Germanium has a half-life of 11.4 days. The radiation outputs of $^{70}$Germanium are photons of 11 keV, which would be very heavily shielded by any source encapsulation. Therefore natural (non-enriched) Germanium could be used for this compound. Other nonmetals may be similarly employed.

Metallic and Nonmetallic Compounds

There exist a number of metals and nonmetals, the neutron irradiation of which does produce products capable of sustained emission of radiation which would acceptably complement the gamma radiation of $^{75}$Selenium, that can be combined with selenium to form a thermally-stable compound or mixture.

For an element to be practical in this regard, the "sustained emission" needs to be "sustained" for a period of time similar to that of $^{75}$Selenium. For purposes of this invention, the half-life of the other isotope or component should be between 25% and 300% of the half-life of $^{75}$Selenium (120 days). Therefore, isotopes with half-lives between 30 and 360 days are acceptable.

Additionally, in order for the emitted radiation to be complementary to that of $^{75}$Selenium, it must have appreciable emission outside the range of energies of $^{75}$Selenium. $^{75}$Selenium principally emits photons between 120 and 401 keV. See FIG. 2A.

Thulium Selenide (TmSe)

Kaldis and Fritzler (Kaldis E and Fritzler B, $A^3$ Solid State Chemistry of New Semiconductors with Valance Instabilities: $TmSe_{1-x}Te_x$ and $Tm_{1-x}Eu_xSe$, J. Phys. Colloques 41 (1980) C5-135-05-142) describe a process for synthesizing TmSe that can be used in the present invention.

Thulium Selenide can also be synthesized by the method described by Matsumura et al. (Takeshi Matsumura, Shintaro Nakamura, Terutaka Goto, Hiroshi Amitsuka, Kazuyuki Matsuhira, Toshiro Sakakibara and Takashi Suzuki, Low Temperature Properties of the Magnetic Semiconductor TmTe, J. Phys. Soc. Jpn. 67 (1998) pp. 612-621). Another description is provided by Grain in U.S. Pat. No. 4,575,464. The melting temperature of TmSe is ~2300° C.

Figure 2B:
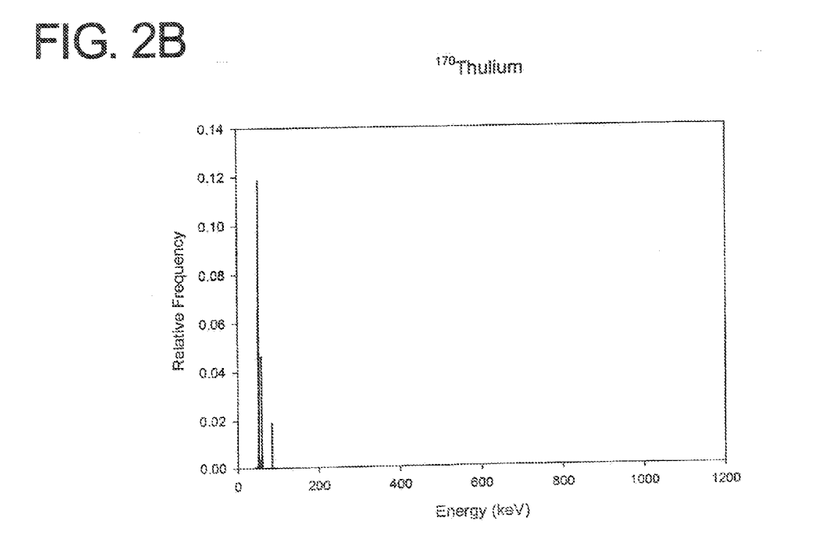
FIG. 2B is graph of the energy spectrum for $^{170}$Thulium.
Figure 2C:
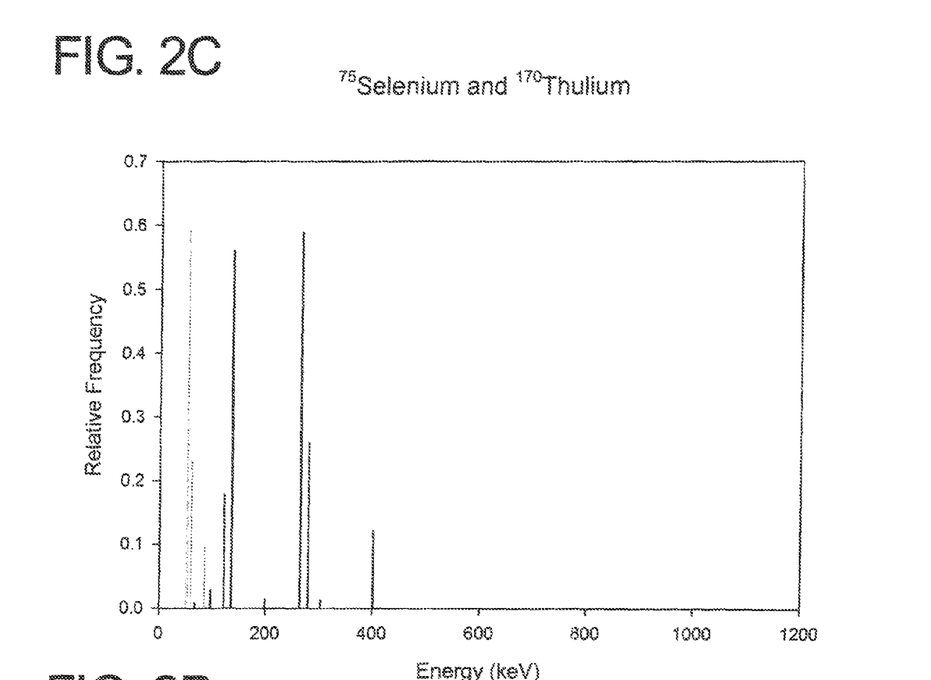
FIG. 2C is graph of the energy spectrum for both $^{75}$Selenium and $^{170}$Thulium illustrating the radiation of $^{170}$Thulium complementing the radiation of $^{75}$Selenium at the lower end of the spectrum.

Thulium, when exposed to neutron irradiation, transmutes into $^{170}$Thulium. This isotope has a half-life of 128 days and emits photons of 48, 49, 51, 52, 55, 57, 59, 60, 78 and 84 keV, see FIG. 2B, which are substantially lower than the photons of $^{75}$Selenium. These lower-energy photons are very complementary to those of $^{75}$Selenium. For example, these would improve the contrast sensitivity of $^{75}$Selenium in the radiographic process. Additionally, $^{170}$Thulium decays by beta emission, and the beta produces bremsstrahlung within the source material itself. In one typical configuration, the average energy of this bremsstrahlung was 74 keV, which is also very complementary. See FIG. 2C which shows that the radiation source of TmSe being located in the lower radiation zone 104 as compared to the primary source of 75Selenium being in the primary zone of 100.

Iridium Selenides

There are three identified selenides of Iridium: $Ir_2Se_3$, $IrSe_2$ and $IrSe_3$. These are prepared by the reaction of Selenium with Iridium Trichloride.

Figure 2D:
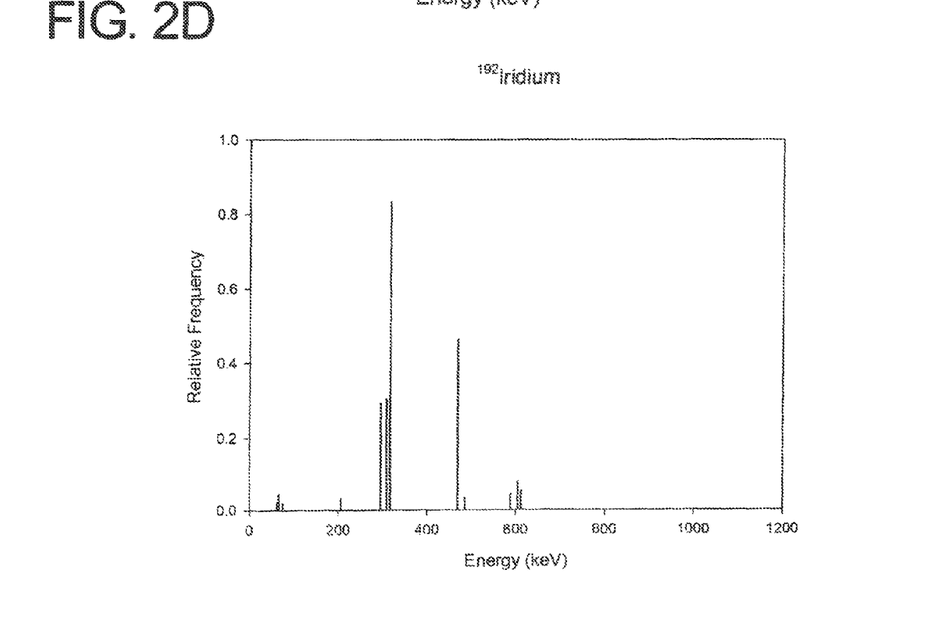
FIG. 2D is graph of the energy spectrum for $^{192}$Iridium.
Figure 2E:
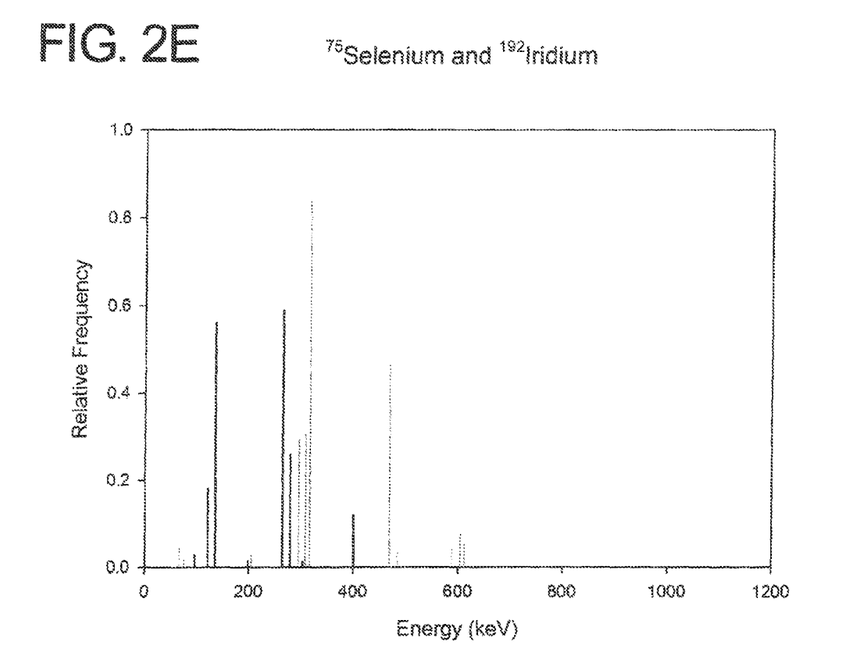
FIG. 2E is graph of the energy spectrum for both $^{75}$Selenium and $^{192}$Iridium illustrating the radiation of $^{192}$Iridium supplementing that of $^{75}$Selenium.

Iridium, when exposed to neutron irradiation, transmutes into $^{192}$Iridium. This isotope has a half-life of 74 days and principally emits photons of ~300, 468, and ~600 keV. See FIG. 2D. Although the ~300 keV photons are within the range of those of $^{75}$Selenium, the other photon emissions are well above those of $^{75}$Selenium. These higher energy photons would be very complementary to those of $^{75}$Selenium. For example, these higher energy photons would extend the useful thickness range in the radiographic process. See FIG. 2E that shows the Iridium source radiation being in the upper radiation zone 106. The Iridium may be of natural isotopic composition or of isotopically modified composition (enriched or depleted in certain isotopes) so that the subsequent radiation peaks may also be adjusted in relative frequency.

Tungsten Diselenide ($WSe_2$)

Tungsten selenide (tungsten diselenide) is commercially available and used as a photovoltaic material in solar cells and other light-to-energy projects, in chemical vapor deposition, sputtering targets, thin-film coatings, and other high-temperature coating and lubricating applications. It has a density of 9.32 mg/mm$^3$. It is reported to have good thermal stability and a high melting point (~1200° C.).

Irradiation of natural tungsten will produce $^{185}$Tungsten ($t_{1/2}$: 75 days; a pure beta emitter), $^{188}$Tungsten ($t_{1/2}$: 69 days; a beta emitter with very little gamma; accompanied by its daughter $^{188}$Rhenium in equilibrium with many high energy gammas from 478 keV to 932 keV, and a small amount of $^{181}$Tungsten ($t_{1/2}$: 121 days; with 56-67 keV x-rays). In an alternative composition, the emission of low energy $^{181}$Tungsten gammas could be enhanced by using some level of enriched $^{180}$Tungsten.

Zinc Selenide (ZnSe)

Figure 2F:
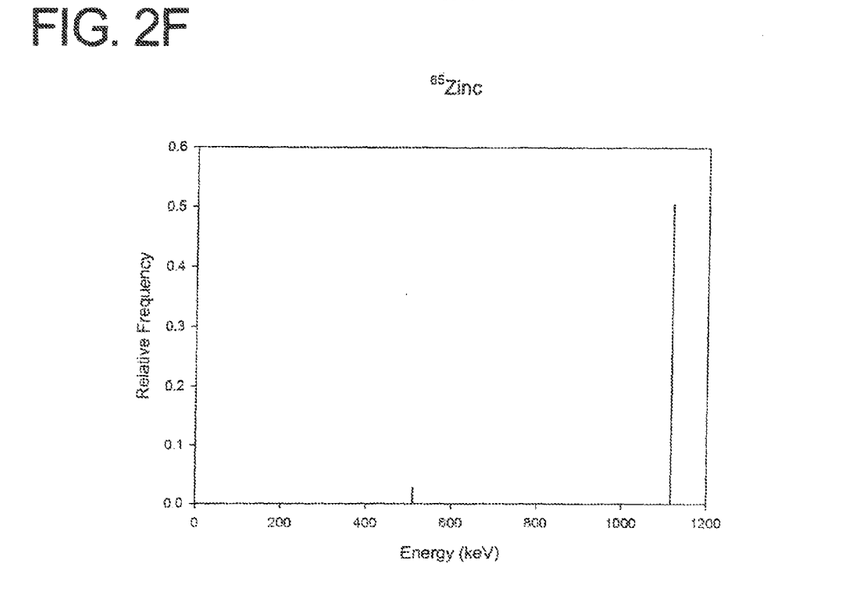
FIG. 2F is graph of the energy spectrum for $^{65}$Zinc.
Figure 2G:
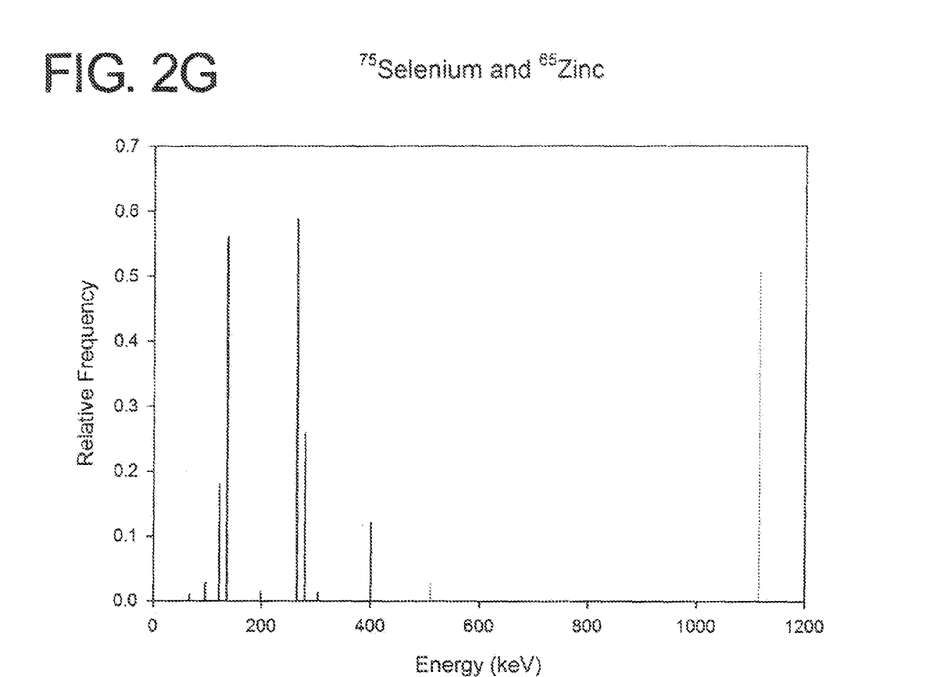
FIG. 2G is graph of the energy spectrum for both $^{75}$Selenium and $^{65}$Zinc illustrating the radiation of $^{65}$Zinc being in the upper energy range.

Zinc selenide (ZnSe), is an intrinsic semiconductor with a melting temperature of >1500° C. Natural Zinc is comprised of approximately 48.9% $^{64}$Zinc, 27.8% of $^{66}$Zinc, 4.1% of $^{67}$Zinc and 18.6% of $^{68}$Zinc and 0.6% of $^{70}$Zinc. When irradiated by neutron flux, $^{64}$Zinc is transmuted to radioactive $^{65}$Zinc which emits high energy gamma rays (1115 keV) and has a half-life of 245 days. These photon emissions are well above those of $^{75}$Selenium. These higher energy photons would be very complementary to those of $^{75}$Selenium. The isotopic composition of Zinc-64 can be enriched up to as high as 99% or depleted to as low as 1% in order to adjust the relative frequency of the radiation peaks. See FIGS. 2A, 2F and 2G. For example, these higher energy photons would extend the useful thickness range in the radiographic process.

Samarium Selenide ($Sm_2Se_3$, $CuSm_3Se_6$, $CuSm_3Se_4$):

Samarium Selenide has a density of 7.33 mg/mm$^3$ and is stable up to at least 1100° C. The only long-lived radionuclide is $^{145}$Sm with a half-life of 340 days and X-rays from 38-44 keV and a 61 keV gamma.

Tantalum Selenide (TaSe, $TaSe_2$) Tantalum selenide (Tantalum diselenide) has a density in the range of 8.5 to 10.2 mg/mm$^3$. It is reported to have good thermal stability up to ~900° C.). Tantalum-182 has a half-life of 115 days and emits a large number of gamma rays between 1100 keV and 1300 keV.

Other Rare Earth Selenides:

Several other rare earth elements (Cerium, Gadolinium, and Ytterbium) form chemically acceptable compounds with Selenium with varying degrees of suitability among the radiological properties.

Other Nonmetallic Selenides:

Antimony Selenide ($Sb_2Se_3$)

Antimony Selenide ($Sb_2Se_3$) (Antimony is another nonmetal metalloid) melts at 617° C. The isotope $^{124}$Antimony, with a half-life of 60.4 days, adds to the spectrum of $^{75}$Selenium a variety of high-energy photons (603 keV, 644 keV, 720 keV, 967 keV, 1.048 MeV, 1.31 MeV, 1.37 MeV, 1.45 MeV, 1.692 MeV, and 2.088 MeV).

The above compounds may be irradiated by neutron bombardment or may be separately irradiated before being combined and thus the radiation spectrum of the compound so formed may be adjusted in relative frequency as would be known by one skilled in the art knowing of the present invention.

Figure 3:
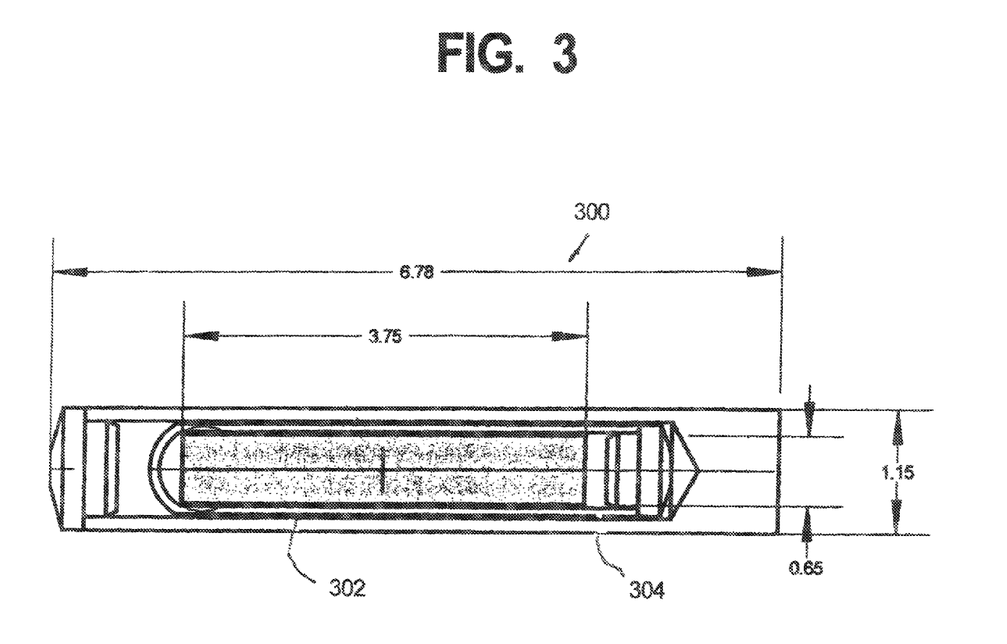
FIG. 3 is across sectional side view of a radiation source within a capsule for use in brachytherapy.

The forming of the above stable compound, alloy, or mixture after irradiation into pellets, beads, etc., would require appropriate shielding and handling. For example, a gamma radiation source 300, FIG. 3, has a cylindrical pellet 302 inserted into a tubular container 304 that may be used in brachytherapy. Clearly other source shapes are possible.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A gamma radiation source comprising: $^{75}$Selenium or a precursor thereof, wherein the $^{75}$Selenium is provided in the form of one or more thermally stable compounds or mixtures, and with one or more nonmetals the neutron irradiation of which does not produce products capable of sustained emission of radiation which would unacceptably interfere with the gamma radiation of $^{75}$Selenium.

2. A gamma radiation source as defined in claim 1, wherein the one or more nonmetals comprise a natural isotopic composition, an enriched isotopic composition, or a depleted isotopic composition.

3. A gamma radiation source comprising: $^{75}$Selenium or a precursor thereof, wherein the $^{75}$Selenium is provided in the form of one or more thermally stable compounds, or mixtures with one or more nonmetals the neutron irradiation of which does not produce products capable of sustained emission of radiation which would unacceptably interfere with the gamma radiation of $^{75}$Selenium, wherein the one or more nonmetals may comprise a natural isotopic composition, an enriched isotopic composition, or a depleted isotopic composition; wherein the gamma radiation peaks of the composition may be adjusted in relative frequency.

4. A gamma radiation source comprising: $^{75}$Selenium or a precursor thereof, wherein the $^{75}$Selenium is provided in the form of one or more thermally stable compounds, or mixtures, and with one or more nonmetals the neutron irradiation of which does not produce products capable of sustained emission of radiation which would unacceptably interfere with the gamma radiation of $^{75}$Selenium, wherein said one or more nonmetals comprises Germanium or Silicon.

5. A gamma radiation source comprising: $^{75}$Selenium or a precursor thereof, wherein the $^{75}$Selenium is provided in the form of one or more thermally stable compounds, or mixtures with one or more nonmetals the neutron irradiation of which does not produce products capable of sustained emission of radiation which would unacceptably interfere with the gamma radiation of $^{75}$Selenium, wherein the one or more nonmetals may comprise a natural isotopic composition, an enriched isotopic composition, or a depleted isotopic composition, wherein said one or more nonmetals comprises Ge or Si, wherein the gamma radiation peaks of the composition may be adjusted in relative frequency.

* * * * *